United States Patent [19]

Merger et al.

[11] Patent Number: 5,118,864
[45] Date of Patent: Jun. 2, 1992

[54] PREPARATION OF CYCLOPENTENONES

[75] Inventors: Franz Merger, Frankenthal; Tom Witzel, Ludwigshafen; Hans Horler, Pfungstadt; Helmut Lermer, Ludwigshafen, all of Fed. Rep. of Germany

[73] Assignee: BASF Aktiengesellschaft, Ludwigshafen, Fed. Rep. of Germany

[21] Appl. No.: 664,382

[22] Filed: Mar. 4, 1991

[30] Foreign Application Priority Data

Mar. 13, 1990 [DE] Fed. Rep. of Germany ....... 4007925

[51] Int. Cl.$^5$ .............................................. C07C 45/45
[52] U.S. Cl. .................................................... 568/356
[58] Field of Search ......................... 568/354, 355, 356

[56] References Cited

U.S. PATENT DOCUMENTS

| | | | |
|---|---|---|---|
| 3,953,514 | 4/1976 | Yamazaki et al. | 568/354 |
| 4,745,228 | 5/1988 | Decker et al. | 568/354 |
| 4,822,920 | 4/1989 | Lermer et al. | 568/355 |

FOREIGN PATENT DOCUMENTS

| | | | |
|---|---|---|---|
| 194144 | 9/1986 | European Pat. Off. | 568/356 |
| 297447 | 6/1988 | European Pat. Off. | 568/354 |
| 0297447 | 1/1989 | European Pat. Off. | 568/355 |
| 2050565 | 4/1971 | Fed. Rep. of Germany | 568/356 |
| 2439742 | 6/1977 | Fed. Rep. of Germany | 568/354 |
| 50-12423 | 6/1975 | Japan | 568/356 |
| 52-118447 | 10/1977 | Japan | 568/356 |
| 54-095535 | 11/1979 | Japan | 568/356 |
| 54-148740 | 11/1979 | Japan | 568/356 |
| 58-162548 | 9/1983 | Japan | 568/354 |
| 58-170728 | 10/1983 | Japan | 568/354 |
| 58-208247 | 12/1983 | Japan | 568/356 |
| 59-80619 | 5/1984 | Japan | 568/356 |
| 62-298547 | 12/1987 | Japan | 568/356 |

OTHER PUBLICATIONS

Org. Synth. Coll. V pp. 326–328, 414–418.
Yukagaku 29 (1980), 920–925.
Chem. Pharm. Bull. 33 (1985) 4798–4802.
Synth. Commun. 9 (1979), 545–552.
Houben-Weyl, vol. 7/2a (1973) 448–457.
Angew. Chem. 96 (1984) 815.
Synthesis (1973) 397–412.
J. Chem. Soc. (1957) 1435–1437.
J. Chem. Soc. (1968) 217–225.
Patent Abstracts of Japan, Unexamined Applications, Section C, vol. 4, No. 12 (C-71).

Primary Examiner—James H. Reamer
Attorney, Agent, or Firm—John H. Shurtleff

[57] ABSTRACT

Cyclopentenones of the formula I

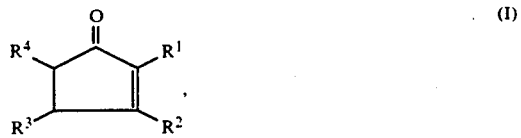

where each of $R^1$ to $R^4$ is independently of the others hydrogen or an organic radical, are prepared by converting a carboxylic ester of the formula IIa, IIb or IIc

| | |
|---|---|
| $R^1CH=CR^2-CHR^3-CHR^4-CO_2R^5$ | (IIa) and/or |
| $R^1CH_2-CR^2=CR^3-CHR^4-CO_2R^5$ | (IIb) and/or |
| $R^1CH_2-CHR^2-CR^3=CR^4-CO_2R^5$ | (IIc), | where each of $R^1$ to $R^4$ is as defined above and $R^5$ is $C_1$–$C_8$-alkyl, over an acidic heterogeneous catalyst at 50°–800° C. and 0.001–50 bar.

14 Claims, No Drawings

PREPARATION OF CYCLOPENTENONES

The present invention relates to a process for preparing 2-cyclopentenones by converting pentenoic esters over acidic heterogeneous catalysts.

Prior art methods for synthesizing cyclopentenone usually start from an existing cyclic carbon structure, for example:

from cyclopentadiene and peracid via epoxycyclopentene (Org. Synth. Coll. V, 326-328, 414-418; Yukagaku 29 (1980), 920-925);

by oxidation of cyclopentene either electrochemically (Chem. Pharm. Bull. 33 (1985), 4798-4802) or with peroxides (e.g. JP 59/80 619); and by dehydrogenation of cyclopentanone (for example over transition metal catalysts, DE-A-20 50 565).

2-Cyclopentenone has been prepared starting from open-chain materials, for example by converting 3-hexene-1,6-dioic esters by means of stoichiometric amounts of strong bases, such as sodium alcoholates, in two stages via the 2-cyclopentene-2-carboxylate intermediate (Dieckmann condensation, e.g. JP 77/118 447). This requires four steps (condensation, neutralization, hydrolysis and decarboxylation), of which the neutralization step inevitably produces an appreciable amount of neutral salts.

Substituted gamma-lactones, obtainable for example from unsaturated carboxylic esters, can be converted with strong acids (sulfuric acid, phosphorus pentoxide) into cyclopentenone derivatives (e.g. Synth. Commun. 9 (1979), 545-552; EP-A-194 144; JP 58/208 247; JP 75/012 423).

It is also known to convert unsaturated carboxylic acids directly into cyclopentenone derivatives in the presence of, for example, sulfuric acid, sulfuric acid/acetic anhydride, zink chloride/acetic anhydride, trifluoroacetic anhydride, phosphorus(V) oxide or phosphorus(V) chloride by intramolecular acylation with elimination of water (Houben-Weyl vol. 7/2a (1973), 448-457; Angew. Chem. 96 (1984), 815; Synthesis 1973, 397-412; JP 54/095 535). JP 54/148 740 describes the gas phase conversion of 4-methylpentenoic acids into 3-methyl-2 cyclopenten-1-one over polyphosphoric acid, silicon dioxide/aluminum oxide or boron phosphate catalysts. These conversions of free, unsaturated carboxylic acids give substituted cyclopentenones in satisfactory or good yields. Unsubstituted 2-cyclopentenone, however, is obtained from pentenoic acid only in traces (J. Chem. Soc. 1957, 1435-1437; J. Chem. Soc. 1968, 217-225).

It is an object of the present invention to provide a commercially attractive, technically simple process for preparing cyclopentenones, in particular for preparing unsubstituted 2-cyclopentenone.

We have found that this object is achieved by a novel process for preparing a cyclopentenone of the formula I

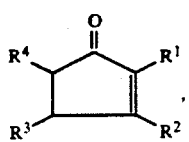
(I)

where each of $R^1$ to $R^4$ is independently of the others hydrogen or an organic radical, comprising reacting a carboxylic ester of the formula IIa, IIb or IIc

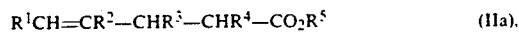
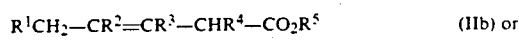
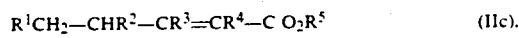

where each of $R^1$ to $R^4$ is as defined above and Rs is $C_1$-$C_8$-alkyl, over an acidic heterogeneous catalyst at 50°-800° C. and 0.001-50 bar.

The reaction may be carried out batchwise or preferably continuously, in the liquid phase or in the gas phase, at 50°-800° C. and 0.001-50 bar.

The liquid phase reaction may be carried out at 50°-200° C. and 0.5-5 bar.

The preferred gas phase reaction may be carried out for example at 150°-800° C. and 0.001-50 bar, preferably at 200°-600° C. and 0.1-5 bar, particularly preferably at 280°-500° C. and 0.5-2 bar. The reaction in the gas phase is advantageously performed at a weight hourly space velocity over the catalyst of from 0.01 to 40, in particular from 0.05 to 10, g of starting material of the formula II per g of catalyst per hour. The gas phase reaction can be carried out in a fixed bed or in a fluidized bed.

After the reaction, the products are isolated from the reaction mixture in a conventional manner, for example by distillation; unconverted starting materials are recycled, where appropriate.

The compounds IIa, IIb and IIc can be used individually or as mixtures, as may be other double bond isomers.

Each of the substituents $R^1$ to $R^4$ is independently of the others hydrogen or an organic radical, such as $C_1$-$C_8$-alkyl, e.g. methyl, ethyl, n-propyl, isopropyl, n-butyl, isobutyl, sec-butyl or tert-butyl, but preferably hydrogen or methyl.

Particularly preferably each of $R^1$ to $R^4$ is hydrogen.

The substituent $R^5$ in compounds II is $C_1$-$C_8$-alkyl, preferably $C_1$-$C_4$-alkyl, such as methyl, ethyl, n-propyl, isopropyl, n-butyl, isobutyl, sec-butyl or tert-butyl, particularly preferably methyl.

Starting compounds of the formulae IIa, IIb and IIc are for example: methyl pentenoate, methyl 4-methylpentenoate, methyl 3-methylpentenoate, methyl 2-methylpentenoate, methyl 2,4-dimethylpentenoate, methyl 2,3-dimethylpentenoate, methyl 3,4-dimethylpentenoate, methyl 2,2-dimethylpentenoate and methyl hexenoate.

End products of the formula I are for example: 2-cyclopenten-1-one, 2-methyl-2-cyclopenten-1-one, 3-methyl-2-cyclopenten-1-one, 4-methyl-2-cyclopenten-1-one, 5-methyl-2-cyclopenten-1-one, 3,5-dimethyl-2-cyclopenten-1-one, 4,5-dimethyl-2-cyclopenten-1-one, 3,4-dimethyl-2-cyclopenten-1-one, 5,5-dimethyl-2-cyclopenten-1-one.

Other products besides cyclopentenones of the formula I are, as a result of retrocarbonylation, dienes of the formula III and their CC double bond isomers

If unsaturated carboxylic esters with $R^1$=alkyl are used, the formation of cyclohexenone derivatives is also possible. For instance, methyl hexenoate ($R^1=R^5=CH_3$, $R^2=R^3=R^4=H$) converts by the process of the present invention into a mixture of 2-methyl-2-cyclopenten-1-one and 2-cyclohexen-1-one in varying proportions.

The process of the present invention is interesting in particular for converting methyl pentenoate mixtures into 2-cyclopentenone (each of $R^1$ to $R^4=H$), since the corresponding pentenoic esters are readily obtainable by carboxylation of butadiene.

Suitable acidic heterogeneous catalysts are in particular acidic zeolites, phosphates or oxides of elements of main groups three and four and subgroups two to six of the periodic table.

It is particularly advantageous to use acidic zeolitic catalysts.

Zeolites are crystalline aluminosilicates which possess a highly ordered structure comprising a rigid three-dimensional network of $SiO_4$ and $AlO_4$ tetrahedra joined together by common oxygen atoms. The ratio of silicon and aluminum to oxygen is 1:2 (see Ullmanns Encyclopädie der technischen Chemie, 4th edition, volume 24, page 575 (1983)). The electrovalence of the aluminum-containing tetrahedra is balanced by the inclusion in the crystal of cations, for example an alkali metal or hydrogen ion. Cation exchange is possible.

The abovementioned tetrahedra, besides silicon and aluminum, may also have incorporated other elements, such as B, Ga, Fe, Cr, V, As, Sb, Be, Ge, Ti, Zr or Hf.

Suitable catalysts for the process of the present invention are zeolites of the mordenite group or narrow-pored zeolites of the erionite or chabazite type or zeolites of the faujasite type, for example Y- or X-zeolites, or L-zeolites. This group of zeolites also includes the ultrastable zeolites of the faujasite type, i.e. dealuminized zeolites. Processes for preparing such zeolites are described in "Catalysis by Zeolites", volume 5 of Studies in Surface Science and Catalysis, ed. B. Imelik et al. Elsevier Scientific Publishing Company, 1980, page 203, and Crystal Structures of Ultrastable Faujasites, Advances in Chemistry Series no. 101, American Chemical Society, Washington D.C., pages 226 ff (1971), and in U.S. Pat. No. 4 512 961.

Of particular advantage are zeolites of the pentasil type. Their common building block is a five-membered ring composed of $SiO_4$ tetrahedra. They are characterized by a high $SiO_2/Al_2O_3$ ratio and by pore sizes between those of zeolites of type A and those of type X or Y (cf. Ullmanns Encyclopädie d. techn. Chem., 4th edition, volume 24, 1983).

These zeolites may have different chemical compositions. They are aluminosilicate, borosilicate, iron silicate, beryllium silicate, gallium silicate, chromium silicate, arsenic silicate, antimony silicate and bismuth silicate zeolites or mixtures thereof and also aluminogermanate, borogermanate, gallium germanate and iron germanate zeolites or mixtures thereof. Of particular suitability for the process of the present invention are the aluminosilicate, borosilicate and iron silicate zeolites of the pentasil type.

The aluminosilicate zeolite is prepared for example from an aluminum compound, preferably $Al(OH)_3$ or $Al_2(SO_4)_3$, and a silicon component, preferably finely divided silicon dioxide, in an aqueous amine solution, in particular in polyamines such as 1,6-hexanediamine or 1,3-propanediamine or triethylenetetramine solution, with or in particular without the addition of alkali metal or alkaline earth metal at from 100 to 220° C under autogenous pressure. This also includes the isotactic zeolites of EP-A-34 727. The aluminosilicate zeolites obtained have an $SiO_2/Al_2O_3$ ratio of from 10 to 40,000, depending on the choice of starting quantities. It is also possible to synthesize such aluminosilicate zeolites in an ether medium, such as diethylene glycol dimethyl ether, in an alcohol medium, such as methanol or 1,4-butanediol, or in water.

The borosilicate zeolite is synthesized for example at from 90° to 200° C. under autogenous pressure by reacting a boron compound, for example $H_3BO_3$, with a silicon compound, preferably finely divided silicon dioxide, in an aqueous amine solution, in particular in 1,6-diaminohexane or 1,3-diaminopropane or triethylenetetramine solution, with or in particular without the addition of an alkali metal or alkaline earth metal. This again includes the isotactic zeolites of EP-A-34 727. Such borosilicate zeolites may likewise be prepared by carrying out the reaction not in an aqueous amine solution but in solution in an ether, for example diethylene glycol dimethyl ether, or in an alcohol, for example 1,6-hexanediol.

The iron silicate zeolite is obtained for example from an iron compound, preferably $Fe_2(SO_4)_3$, and a silicon compound, preferably finely divided silicon dioxide, in an aqueous amine solution, in particular 1,6-diaminohexane, with or without the addition of an alkali metal or alkaline earth metal, at from 100° to 220° C. under autogenous pressure.

The usable silicon-rich zeolites ($SiO_2/Al_2O_3 \geq 10$) also include the ZSM types, ferrierite, NU-1 and Silicalite ® (a molecular sieve as described in U.S. Pat. No. 4 061 724).

After the aluminosilicate, borosilicate and iron silicate zeolites have thus been prepared and isolated, dried at 100°-160° C., preferably 110° C., and calcined at 450°-550° C., preferably 500° C., they may be molded with a binder in a ratio of from 90:10 to 40:60% by weight into strands or tablets. Suitable binders are various aluminum oxides, preferably boehmite, amorphous alumino-silicates having an $SiO_2/Al_2O_3$ ratio of from 25:75 to 95:5, preferably 75:25, silicon dioxide, preferably finely divided $SiO_2$, mixtures of finely divided $SiO_2$ and finely divided $Al_2O_3$, $TiO_2$, $ZrO_2$ and clay. After molding, the extrudates or pellets are dried at 110° C. for 16 hours and calcined at 500° C., again for 16 hours.

Advantageous catalysts are also obtained on molding the isolated aluminosilicate or borosilicate zeolite directly after drying and calcining it only after it has been molded. The synthesized aluminosilicate and borosilicate zeolites can be used in pure form, without binder, as strands or tablets, in which case the extruding or peptizing aids used are for example ethylcellulose, stearic acid, potato starch, formic acid, oxalic acid, acetic acid, nitric acid, ammonia, amines and graphite or mixtures thereof.

If the as-prepared zeolite is not in the catalytically active, acidic H-form but for example in the Na-form, it can be completely or partially converted into the desired H-form by ion exchange, for example with ammonium ions, and subsequent calcination or by treatment with an acid.

If in the course of use for the purposes of the present invention the zeolitic catalyst should become deactivated due to coking, it is advisable to regenerate it by burning off the coke deposit with air or with an air/$N_2$ mixture at from 400° to 550° C., preferably at 500° C. This restores the zeolite to its initial activity.

By partial precoking it is possible to optimize the selectivity of the catalyst for the desired reaction product.

To obtain maximum selectivity, high conversion and long catalyst lives, it is advantageous to modify the zeolites. A suitable modification of the catalysts comprises for example doping the molded or unmolded zeolites with metal salts by ion exchange or by impregnation. The metals used are alkali metals such as Li, Cs and K, alkaline earth metals such as Mg, Ca and Ba, metals of subgroups 3, 4 and 5 such as Al, Ga, Sn, Pb and Bi, transition metals of subgroups 4 to 8, such as Ti, Zr, V, Nb, Cr, Mo, W, Mn, Re, Fe, Ru, Os, Co, Rh, Sr, Ni, Pd and Pt, transition metals of subgroups 1 and 2 such as Cu, Ag and Zn and rare earth metals such as La, Ce, Pr, Nd, Yb and U.

Advantageously, such doping is effected for example by introducing the molded zeolite into a riser pipe and passing for example an aqueous or ammoniacal solution of a halide or nitrate of one of the above-described metals over it at 20°-100° C. Such ion exchange can be effected for example on the hydrogen, ammonium or alkali metal form of the zeolite. A further way of applying a metal to the zeolite comprises for example impregnating the zeolitic material with a halide, a nitrate or an oxide of one of the above-described metals in an aqueous, alcoholic or ammoniacal solution. Both ion exchange and impregnation are followed by at least one drying operation, or alternatively by a further calcination.

A possible embodiment comprises for example dissolving $Cu(NO_3)_2 \times 3\ H_2O$ or $Ni(NO_3) \times 6\ H_2O$ or $Ce(NO_3)_3 \times 6\ H_2O$ or $La(NO_3) \times 6\ H_2O$ or $Cs_2CO_3$ in water. This solution is used to impregnated the molded or unmolded zeolite for a certain time, say 30 minutes. Any supernatant solution is stripped of water in a rotary evaporator. Thereafter the impregnated zeolite is dried at about 150° C. and calcined at about 550° C. This impregnation can be carried out repeatedly in succession in order to instill the desired metal content.

It is also possible to prepare for example an aqueous $Ni(CO_3)_2$ solution or an ammoniacal $Pd(NO_3)_2$ solution and to suspend the pure pulverulent zeolite therein at 40°-100° C. by stirring for about 24 hours. Following filtration, drying at about 150° C. and calcination at about 500° C. the zeolitic material thus isolated can be further processed with or without binders into strands, pellets or fluidizable material.

An ion exchange with the zeolite in H-form, ammonium form or alkali metal form can be effected by introducing the zeolite into a column in strand or pellet form and recirculating for example an aqueous $Ni(NO_3)_2$ solution or ammoniacal $Pd(NO_3)_2$ solution through it at a slightly elevated temperature of from 30° to 80° C. for 15-20 hours. This is followed by washing with water, drying at about 150° C. and calcining at about 550° C. With some metal-doped zeolites, for example Pd-, Cu- and Ni-doped zeolites, an aftertreatment with hydrogen is advantageous.

A further modifying technique comprises subjecting the zeolitic material in the molded or unmolded state to a treatment with an acid such as hydrochloric acid, hydrofluoric acid or phosphoric acid and/or steam. Advantageously, for example, the zeolite is treated in powder form with 1 N phosphoric acid at 80° C. for 1 hour. After this treatment, it is washed with water, dried at 110° C. for 16 hours and calcined at 500° C. for 20 hours. Alternatively, the zeolite, before or after it has been molded with a binder, is treated for example at 60°-80° C. with a 3-25% strength by weight, in particular a 12-20% strength by weight, hydrochloric acid solution for 1-3 hours. Thereafter the zeolite thus treated is washed with water, dried and calcined at 400°-500° C.

A particular form of the acid treatment comprises treating the unmolded zeolitic material at elevated temperature with hydrofluoric acid, in general in the form of 0.001-2 N, preferably 0.05-0.5 N, hydrofluoric acid, for example by refluxing for in general 0.5-5, preferably 1-3, hours. After the zeolitic material has been isolated, for example by filtration and washing, it is advantageously dried, for example at 100°-160° C., and calcined, in general at 450°-600° C. In another preferred form of the acid treatment, the zeolitic material is molded with a binder and then treated at elevated temperature, advantageously at 50°-90° C., preferably 60°-80° C., with 12-20% strength by weight hydrochloric acid for 0.5-5 hours. Then the zeolitic material is in general washed and advantageously dried, for example at 100°-160° C. and calcined, in general at 450°-600° C. An HF treatment can also be followed by an HCl treatment.

Alternatively, zeolites may be modified by applying phosphorus compounds, such as trimethyl phosphate, trimethoxyphosphine or primary, secondary or tertiary sodium phosphate. The treatment with primary sodium phosphate is particularly advantageous. It involves impregnating the zeolite in strand, tablet or fluidizable form with aqueous $NaH_2PO_4$ solution, drying at 110° C. and calcining at 500° C.

Suitable acidic heterogeneous catalysts also include phyllosilicates such as montmorillonite and bentonite.

Further catalysts for the process of the present invention are phosphates, in particular aluminum phosphates, silicon aluminum phosphates, silicon iron aluminum phosphates, cerium phosphates, zirconium phosphates, boron phosphates, iron phosphates and mixtures thereof.

The aluminum phosphate catalysts used for the process of the present invention are in particular aluminum phosphates synthesized under hydrothermal conditions. It is possible to use for example $AlPO_4$, SAPO, MeAPO, MeAPSO, ElAPO and ElAPSO (see E. M. Flanigen et al. Pure & Appl. Chem. 58 (1986), 1351) and also aluminum phosphates of the MCM type.

Boron phosphates for the process of the present invention can be prepared for example by mixing and kneading concentrated boric acid and by subsequent drying and calcination in an inert gas, air or steam atmosphere at from 250° to 650° C., preferably from 300°-to 500° C.

Phosphate catalysts usable in the process also include precipitated aluminum phosphates. Such an aluminum phosphate is prepared for example by dissolving 92 g of diammonium hydrogen phosphate in 700 ml of water, adding 260 g of $Al(NO_3)_3 \times H_2O$ in 700 ml of water dropwise over 2 h while the pH is maintained at 8 by the simultaneous addition of 25% strength $NH_3$ solution, stirring for 12 h, filtering off with suction, washing and drying at 60° C. for 16 h.

A cerium phosphate usable for the process of the present invention is obtained for example by precipitating 52 g of $Ce(NO_3)_3 \times 6\ H_2O$ and 56 g of $NaH_2PO_4 \times 2\ H_2O$. After filtration, the material is molded into strands, dried at 120° C. and calcined at 450° C.

These phosphates may be modified by impregnation (soaking and spraying) or in some cases also by ion exchange in the same way as described above for the zeolites. Similarly, as with the zeolite catalysts, they may be modified with an acid, for example phosphoric acid.

A phosphoric acid-containing catalyst may be obtained for example by impregnating a carrier such as $SiO_2$ with $Na_3PO_4$ or $NaH_2HPO_4$ or $Na_2HPO_4$ solution and then drying or calcining. However, phosphoric acid can also be sprayed together with silica gel into a spray tower and then dried and usually calcined. Phosphoric acid can also be sprayed onto the carrier material in an impregnating mill.

Advantageous catalysts for the process of the present invention also include acidic oxides, for example those of elements of main groups three and four and subgroups two to six of the periodic table, in particular oxides such as silicon dioxide in the form of silica gel, diatomaceous earth and quartz, but also zinc oxide, titanium dioxide, zirconium dioxide, phosphorus oxides, vanadium oxides, niobium oxides, boron oxides, aluminum oxides, chromium oxides, molybdenum oxides, tungsten oxides, pumice and mixtures thereof. Mixtures of the aforementioned oxides are for example aluminum oxide such as gamma-$Al_2O_3$ with boron oxide, silicon dioxide, tungsten oxide or chromium oxide. The oxides may be doped with modifying components applied as described above for zeolite catalysts. The acid treatment described for the zeolite catalysts is another possible modifying technique.

The catalysts described herein may as a matter of choice be used in the form of strands from 2 to 4 mm in length or in the form of tablets from 3 to 5 mm in diameter or in the form of chips 0.05 mm, in particular from 0.1 to 0.5 mm, in particle size or in fluidizable form. The fluidizable material may be produced for example by strand comminution and classification or else by spray drying.

The advantageous result of the process of the present invention was not foreseeable from the prior art. On the contrary, the literature reveals that in the presence of acidic heterogeneous catalysts carboxylic esters are converted in the gas phase with elimination of the carboxyl function into saturated and in particular unsaturated hydrocarbons (for example EP-A-135 436, U.S. Pat. No. 4 102 938, JP 50/47904).

Cyclopentenones are useful intermediates for synthesizing scents and natural substances, including prostaglandins. The $\alpha,\beta$-unsaturated ketone system of the 2-cyclopentenones permits a multiplicity of addition reactions of the Michael or Diels-Alder type.

EXAMPLE 1

Preparation of catalyst

An aluminosilicate zeolite of the pentasil type was prepared hydrothermally under autogenous pressure and at 150° C. from 650 g of finely divided $SiO_2$ and 203 g of $Al_2(SO_4)_3 \times 18\ H_2O$ in 10 kg of an aqueous 1,6-diaminohexane solution (mixture 50:50% by weight) in a stirred autoclave. The crystalline reaction product was filtered off, washed, dried at 110° C. for 24 h and calcined at 500° C. for 24 h. This aluminosilicate zeolite contained 92.8% by weight of $SiO_2$ and 4.2% by weight of $Al_2O_3$.

To prepare the catalyst the alusilicate zeolite was treated with HF by boiling 50 g of the alusilicate zeolite under reflux with a mixture of 140 ml of 0.1 N HF and 40 ml of water. After filtration the product was washed neutral with water, dried at 110° C. for 16 h and calcined at 500° C. for 5 h. This material was extruded with amorphous aluminosilicate ($SiO_2$: $Al_2O_3$ = 75:25% by weight) in a weight ratio of 60:40. It was then dried at 110° C. for 16 h and calcined at 500° C. for 16 h.

Preparation of 2-cyclopenten-1-one from methyl 3-pentenoate 49.8 g of methyl 3-pentenoate (cis/trans mixture) per hour were vaporized under atmospheric pressure and passed at 450° C. over the above catalyst (bed density 0.52 kg per liter, internal diameter of reactor 25 mm). The weight hourly space velocity was 0.50 kg of ester per liter of catalyst per hour and the inert gas rate was 50 l of nitrogen per liter of catalyst per hour. The resulting vapors were condensed. A period of 2 hours produced 86.6 g of a mixture which according to quantitative gas chromatography contained 13.1% by weight of methyl 2-pentenoate, 51.8% by weight of methyl 3-pentenoate, 3.6% by weight of methyl 4-pentenoate and 14.1% by weight of cyclopentenone. This corresponds to a total methyl pentenoate conversion of 40.4% and a 2-cyclopentenone selectivity of 42.2%.

EXAMPLE 2

Preparation of catalyst

A borosilicate zeolite of the pentasil type was prepared in a hydrothermal synthesis from 640 g of finely divided $SiO_2$, 122 g of $H_3BO_3$ and 8,000 g of a 50% strength aqueous 1,6-diaminohexane solution at 170° C. under autogenous pressure in a stirred autoclave. After filtration and washing, the crystalline reaction product was dried at 100° C. for 24 hours and calcined at 500° C. for 24 hours. This borosilicate zeolite contains 94.2% by weight of $SiO_2$ and 2.3% by weight of $B_2O_3$.

This material was extruded with a molding aid into 2-mm strands which were dried at 110° C for 16 hours and calcined at 500° C. for 24 hours.

Preparation of 2-cyclopenten-1-one from methyl 3-pentenoate 32.5 g of methyl 3-pentenoate per hour were vaporized under atmospheric pressure and passed at 450° C. over the borosilicate zeolite (bed density 0.37 kg, internal diameter of reactor 20 mm). A weight hourly space velocity of 0.50 kg of ester per liter of catalyst per hour and an inert gas rate of 77 l of nitrogen per liter of catalyst per hour produced in 2 hours 52.8 g of a product mixture which according to quantitative gas chromatography contained 6.2% by weight of methyl 2-pentenoate, 10.0% by weight of methyl 3-pentenoate, 3.5% by weight of methyl 4-pentenoate and 34.0% by weight of 2-cyclopentenone. This corresponds to a cyclopentenone selectivity of 45.7% and a total methyl pentenoate conversion of 84.0%.

EXAMPLE 3

Preparation of catalyst

A cesium-containing borosilicate zeolite was obtained by impregnating the borosilicate zeolite strands of Example 2 with an aqueous $Cs_2CO_3$ solution, then drying at 130° C. for 2 hours and calcining at 540° C., again for 2 hours. The Cs content was 0.6% by weight.

Preparation of 2-cyclopenten-1-one from methyl 3-pentenoate

Methyl 3-pentenoate was vaporized at 255° C. under atmospheric pressure and passed at 450° C. over 100 ml of the cesium-doped borosilicate zeolite (bed density 0.40 kg per liter, internal diameter of reactor 25 mm). A weight hourly space velocity of 0.51 kg of ester per liter of catalyst per hour and an inert gas rate of 100 l of nitrogen per liter of catalyst per hour produced in the course of 5 hours 199.6 g of a condensed product mixture of the following composition: 6.6% by weight of methyl 2-pentenoate, 10.1% by weight of methyl 3-pentenoate, 3.4% by weight of methyl 4-pentenoate and 36.8% by weight of 2-cyclopentenone, corresponding to a cyclopentenone selectivity of 47.4% and a total pentenoic ester conversion of 84.3%.

EXAMPLE 4

Preparation of 2-cyclopenten-1-one from methyl 2-pentenoate

Methyl 2-trans-pentenoate was vaporized in a quartz tube under atmospheric pressure at a rate of 50.0 g per hour and passed together with 10 l of nitrogen over 100 ml of a cesium-doped borosilicate zeolite of Example 3 (bed density 0.40 kg per liter, internal diameter of reactor 25 mm) at 450° C.; the reaction vapors were condensed. Over 4 hours this produced 158.7 g of a mixture of the following composition: 0.6% by weight of methyl 2-pentenoate, 1.2% by weight of methyl 3-pentenoate, 1.3% by weight of methyl 4-pentenoate and 39.8% by weight of cyclopentenone; this corresponds to a total methyl pentenoate conversion of 97.5% and a 2-cyclopentenone selectivity of 45.1%.

EXAMPLE 5

Preparation of 2-cyclopentenone from methyl 4-pentenoate

Methyl 4-pentenoate was vaporized under atmospheric pressure at a rate of 47.2 g per hour and passed together with 10 l of nitrogen into a hot reactor (internal diameter 25 mm) at 450° C. packed with 100 ml of the cesium-doped borosilicate zeolite of Example 3. The reaction vapors were condensed to produce over a period of 2 hours 88.8 g of a mixture of the following composition (quantitative GC): 6.4% by weight of methyl 2-pentenoate, 11.2% by weight of methyl 3-pentenoate, 11.4% by weight of methyl 4-pentenoate and 32.6% by weight of 2-cyclopentenone, corresponding to a total methyl pentenoate conversion of 72.7% and a 2-cyclopentenone selectivity of 58.6%.

EXAMPLE 6

Preparation of 3-methyl-2-cyclopenten-1-one from methyl 4-methyl-4-pentenoate

Methyl 4-methyl-4-pentenoate was vaporized under atmospheric pressure at a rate of 22.2 g per hour and passed together with 5 liters of nitrogen through a hot reactor (internal diameter 25 mm) at 350° C. which was packed with 50 ml of the cesium-doped borosilicate zeolite of Example 3. The reaction vapors were condensed. This produced over 2.5 hours 53.7 g of a reaction mixture comprising 0.6% by weight of methyl 4-methyl-4pentenoate and 55.1% by weight of 3-methyl-2-cyclo-penten-1-one, corresponding to a selectivity of 71.2% and a conversion of 99.4%.

EXAMPLE 7

Preparation of 2-methyl-2-cyclopenten-1-one and 2-cyclohexen-1-one from methyl hexenoate Methyl hexenoate (a double bond isomer mixture containing 55% of the 5-ester and 37% of the 4-ester) was passed at a rate of 27.4 g per hour together with 5 liters of nitrogen through a reactor (internal diameter 25 mm) packed with 50 ml of the cesium-doped borosilicate zeolite of Example 3. Condensation of the reaction vapors over 4 hours gave 105.1 g of a mixture which according to quantitative gas chromatography contained 8.8 g of methyl hexenoate (isomer mixture), 25.2 g of 2-methyl-2-cyclo-penten-1-one and 28.8 g of 2-cyclohexen-1-one, corresponding to a hexenoate conversion of 92.0% and selectivities of 33.3% for 2-methylcyclopentenone and 38.1% for cyclohexenone.

EXAMPLE 8

Preparation of 2-methyl-2-cyclopenten-1-one and 2-cyclohexen-1-one from methyl hexenoate Methyl hexenoate (double bond isomer mixture containing 55% of the 5-ester and 37% of the 4-ester) was vaporized under atmospheric pressure at a rate of 48.9 g per hour and passed together with 10 l of nitrogen into a hot reactor (internal diameter 25 mm) at 450° C. packed with 100 ml of the cesium-doped borosilicate zeolite of Example 3. Condensation of the reaction vapors over a 3 hour period produced 139.0 g of a mixture of the following composition (quantitative GC): 1.3% by weight of hexenoate (isomer mixture), 29.4% by weight of 2-methyl-2-cyclopenten-1-one and 19.4% by weight of 2-cyclohexen-1-one, corresponding to a conversion of 98.8% and selectivities of 37.5% for 2-methylcyclopentenone and 24.8% for cyclohexenone.

We claim:

1. A process for preparing a cyclopenenone of the formula I

where each of $R^1$ and $R^4$ is independently of the others hydrogen or an organic radical, comprising converting a carboxylic ester of the formula IIa, IIb or IIc $$R^1CH=CR^2-CHR^3-CHR^4-CO_2R^5 \quad \text{(IIa)},$$

$$R^1CH_2-CR^2=CR^3-CHR^4-CO_2R^5 \quad \text{(IIb) or}$$

$$R^1CH_2-CHR^2-CR^3=CR^4-CO_2R^5 \quad \text{(IIc)},$$

where each of $R^1$ to $R^4$ is as defined above and $R^5$ is $C_1$-$C_8$-alkyl, over an acidic heterogeneous catalyst selected from the group consisting of the zeolites, phosphates and oxides of elements of main groups 3 and 4 and subgroups 2, 3, 4, 5 and 6 of the periodic table, the reaction being carried out at 50°–800° C. and 0.001–50 bar.

2. A process as claimed in claim 1, wherein the substituents $R^1$ to $R^4$ are each independently of the others hydrogen or $C_1$-$C_8$-alkyl.

3. A process as claimed in claim 1, wherein the substituents $R^1$ to $R^4$ are each independently of the others hydrogen or $C_1$-$C_4$-alkyl.

4. A process as claimed in claim 1, wherein the substituents $R^1$ to $R^4$ are each independently of the others hydrogen or methyl.

5. A process as claimed in claim 1, wherein the substituent $R^5$ in the formula II is $C_1$-$C_4$-alkyl.

6. A process as claimed in claim 1, wherein the substituent $R^5$ in the formula II is methyl.

7. A process as claimed in claim 1, wherein the reaction is carried out in the gas phase at 150°-800° C. and 0.001-50 bar.

8. A process as claimed in claim 1, wherein the reaction is carried out over a acidic zeolitic catalyst.

9. A process as claimed in claim 1, wherein the reaction is carried out over an aluminosilicate zeolite of the pentasil type as the catalyst.

10. A process as claimed in claim 1, wherein the reaction is carried out over a borosilicate zeolite of the pentasile type as the catalyst.

11. A process as claimed in claim 1, wherein the reaction is carried out over a borosilicate zeolite of the pentasil type as the catalyst which has been doped with cesium.

12. A process as claimed in claim 1 wherein the substituents $R^1$ to $R^4$ are each hydrogen and $R^5$ is $C_1$-$C_4$-alkyl.

13. A process as claimed in claim 1 wherein the substituents $R^1$ to $R^4$ are each hydrogen and $R^5$ is methyl.

14. A process as claimed in claim 1 wherein $R^1$ is methyl, the substituents $R^2$ to $R^4$ are each hydrogen, and $R^5$ is methyl.

* * * * *